United States Patent
Kajimoto et al.

(10) Patent No.: US 9,968,704 B2
(45) Date of Patent: May 15, 2018

(54) METHOD FOR REGENERATING ALVEOLAR BONE AND CALCIUM-CONTAINING MICROPARTICLES USED TO REGENERATE ALVEOLAR BONE

(75) Inventors: Naoko Kajimoto, Mizuho (JP);
Kyousuke Kajimoto, Mizuho (JP);
Tadamori Kajimoto, Mizuho (JP)

(73) Assignee: BIO MAP CO., LTD., Mizuho-Shi, Gifu (JP)

( * ) Notice: Subject to any disclaimer, the term of this patent is extended or adjusted under 35 U.S.C. 154(b) by 717 days.

(21) Appl. No.: 14/395,063

(22) PCT Filed: Apr. 19, 2012

(86) PCT No.: PCT/JP2012/060566
§ 371 (c)(1),
(2), (4) Date: Feb. 23, 2015

(87) PCT Pub. No.: WO2013/157112
PCT Pub. Date: Oct. 24, 2013

(65) Prior Publication Data
US 2015/0165088 A1 Jun. 18, 2015

(51) Int. Cl.
*A61L 27/02* (2006.01)
*A61C 8/02* (2006.01)
(Continued)

(52) U.S. Cl.
CPC .......... *A61L 27/025* (2013.01); *A61C 8/0006* (2013.01); *A61L 27/12* (2013.01);
(Continued)

(58) Field of Classification Search
CPC ......... A61L 27/025; A61B 2018/00577; A61C 1/00; A61C 1/0061
See application file for complete search history.

(56) References Cited

U.S. PATENT DOCUMENTS

| | | | |
|---|---|---|---|
| 2005/0163861 A1* | 7/2005 | Epple | A61L 27/46 424/549 |
| 2011/0020419 A1 | 1/2011 | Yuan et al. | |
| 2012/0065741 A1* | 3/2012 | Chang | A61C 8/0006 623/23.72 |

FOREIGN PATENT DOCUMENTS

| | | |
|---|---|---|
| EP | 1520593 A1 | 4/2005 |
| JP | 2000-500110 | 1/2000 |

(Continued)

OTHER PUBLICATIONS

Notice of Reasons for Rejection, dated Feb. 9, 2016, issued in Japanese Patent Application No. 2014-511037, 6 pages.

(Continued)

*Primary Examiner* — Thomas J Sweet
*Assistant Examiner* — Daniel Bissing
(74) *Attorney, Agent, or Firm* — Nixon Peabody LLP; Jeffrey L. Costellia

(57) ABSTRACT

A method for regenerating alveolar bone in which bone tissue is regenerated in the gap between an implant or dental root and alveolar bone, which comprises a procedure consisting of making an incision in the gingiva surrounding an implant or dental root embedded in alveolar bone, blowing a first air into the gap between the implant or dental root and the alveolar bone to remove a portion of infected granulation tissue present in the gap, and irradiating the gap with laser light to degenerate the infected granulation tissue remaining in the gap, followed by blowing a second air containing microparticles having calcium as a constituent thereof and water into the gap to remove the degenerated infected granulation tissue and fill in the gap with the wet microparticles.

9 Claims, 8 Drawing Sheets

(51) Int. Cl.
- *A61L 27/12* (2006.01)
- *A61L 27/54* (2006.01)
- *A61B 18/00* (2006.01)
- *A61B 18/20* (2006.01)
- *A61N 5/06* (2006.01)

(52) U.S. Cl.
CPC ............... *A61L 27/54* (2013.01); *A61B 18/20* (2013.01); *A61B 2018/00577* (2013.01); *A61L 2400/06* (2013.01); *A61L 2430/12* (2013.01); *A61N 5/062* (2013.01)

(56) References Cited

FOREIGN PATENT DOCUMENTS

| | | |
|---|---|---|
| JP | 2004-113625 | 4/2004 |
| JP | 2006136457 A | 6/2006 |

OTHER PUBLICATIONS

Extended European Search Report issued in EP Patent Application No. 12874604.7 dated Nov. 26, 2015, 7 pgs.

Fujisawa, Kenji, et al., "Teikesshosei Tansan Apatite no Gakukotsu Saiken eno Oyoni Kansuru Kisoteki Kenkyu, the 5th report: Karyukei ga Tansan Apatite no Kyushuto Hone Keisei ni Oyobosu Eikyo",Dai 32 Kai the Annual Meeting of the Japanese Society for Biomaterials Yokoshu, Nov. 29, 2010, p. 368 (p. 2-98).

Patel N., et al, Preparation and Characterisation of Hydroxyapatite and CarbonateSubstituted Hydroxyapatite Granules,Key Engineering Materials, 2001, vols. 192-195, pp. 7-10.

Yamamoto, Atsuhiko, et al., "Er : YAG Laser no Implant Shuien eno Oyo", Journal of Japanese Society for Laser Dentistry, 2009, vol. 20, pp. 81 to 87.

International Search Report for PCT/JP2012/060566 dated Jun. 19, 2012.

* cited by examiner

METHOD FOR REGENERATING ALVEOLAR BONE AND CALCIUM-CONTAINING MICROPARTICLES USED TO REGENERATE ALVEOLAR BONE

CROSS-REFERENCE TO RELATED PATENT APPLICATIONS

The present application is a National Stage Application of International Application No. PCT/JP2012/060566 entitled "METHOD FOR REGENERATING ALVEOLAR BONE AND CALCIUM-CONTAINING MICROPARTICLES USED TO REGENERATE ALVEOLAR BONE" filed Apr. 19, 2012, the contents of which is incorporated herein by reference in their entirety.

TECHNICAL FIELD

The present invention relates to a method for regenerating alveolar bone and calcium-containing microparticles used to regenerate alveolar bone.

BACKGROUND ART

A series of treatments in the form of a so-called implant procedure, consisting of surgically embedding a pin-shaped implant (artificial tooth) in alveolar bone (jawbone) followed by attaching an artificial crown and upper structure, is performed for the purpose of replacing the function of a lost tooth. This type of implant procedure differs from a bridge or plate denture in that function and form are attempted to be restored that closely match the inherent state of the tooth while also offering the advantage of eliminating the need to drill surrounding teeth.

Infected granulation tissue may be formed between alveolar bone and an implant that has been embedded for a long period of time due to the effects of periodontal disease and other conditions, resulting in loosening of the immobilized implant. In this case, it is necessary to surgically remove the infected granulation tissue and re-immobilize the implant in alveolar bone. In order to adequately immobilize an implant, a treatment period is normally required to regenerate bone tissue between the implant and alveolar bone. Since the patient is forced to use a temporary denture or be hospitalized for the purpose of observation during this treatment period, resulting in the patient being subjected to various inconveniences and burdens, it is desired to shorten this treatment period. A known example of a conventional method consists of the application of ultrasonic vibrations to the treatment site (treated area) to promote regeneration of bone tissue, and the use of an ultrasonic therapy apparatus (Patent Document 1).

PRIOR ART DOCUMENTS

Patent Documents

Patent Document 1: Japanese Unexamined Patent Application, First Publication No. 2004-113625

DISCLOSURE OF THE INVENTION

Problems to be Solved by the Invention

Treatment with an ultrasonic therapy apparatus is a method for promoting formation of bone tissue by enhancing the activity of cells responsible for bone metabolism (osteoblasts and osteoclasts) by ultrasonic treatment. According to this method, although the treatment period can be shortened to a certain degree, further shortening of the treatment period is desired.

In consideration of the aforementioned circumstances, an object of the present invention is to provide a method for regenerating alveolar bone that is able to shorten the treatment period by promoting the formation of bone tissue between an implant or dental root and alveolar bone, and calcium-containing microparticles used in that regeneration method.

Means for Solving the Problems

The calcium-containing microparticles for regenerating alveolar bone of the present invention are calcium-containing microparticles used in a method for regenerating alveolar bone comprising a procedure consisting of making an incision in the gingiva surrounding an implant or dental root embedded in alveolar bone, blowing a first air containing the calcium-containing microparticles into a gap between the implant or dental root and the alveolar bone to remove a portion of infected granulation tissue present in the gap and expose at least a portion of the surface of the implant or dental root, and irradiating the surface and the microparticles with laser light in a state in which the microparticles are adhered to at least a portion of the surface to fix at least a portion of the microparticles to the surface and degenerate the infected granulation tissue remaining in the gap, followed by blowing a second air containing the microparticles and water into the gap to remove the degenerated infected granulation tissue and fill in the gap with the wet microparticles; wherein, the microparticles are obtained by crushing clumps of raw material composed of carbonate apatite followed by recovering those microparticles among the resulting microparticles that pass through a sieve having a mesh size of 500 μm but do not pass through a sieve having a mesh size of 300 μm.

Use of the calcium-containing microparticles according to the present invention makes it possible to promote regeneration of bone tissue of alveolar bone and shorten the treatment period thereof.

The method for regenerating alveolar bone of the present invention is a method for regenerating alveolar bone in which bone tissue is regenerated in the gap between an implant or dental root and alveolar bone, comprising a procedure consisting of making an incision in the gingiva surrounding an implant or dental root embedded in alveolar bone, blowing a first air into a gap between the implant or dental root and the alveolar bone to remove a portion of infected granulation tissue present in the gap, and irradiating the gap with laser light to degenerate the infected granulation tissue remaining in the gap, followed by blowing a second air containing microparticles having calcium as a constituent thereof and water into the gap to remove the degenerated infected granulation tissue and fill in the gap with the wet microparticles.

According to this method, by degenerating small fragments (thin pieces) of infected granulation tissue adhered to the surface of an exposed implant or dental root, which are comparatively difficult to remove by blowing the first air alone, by irradiating with laser light, the infected granulation tissue can be completely removed. Since infected granulation tissue readily serves as a hotbed for bacterial growth, it is important to completely remove the infected granulation tissue without leaving any behind. In this manner, since cells that form bone tissue can be easily activated by cleaning gaps between an implant or dental root and alveolar bone, regeneration of alveolar bone can be accelerated.

The method for regenerating alveolar bone of the present invention is the method, wherein together with containing the microparticles in the first air and blowing the first air into the gap to remove a portion of infected granulation tissue present in the gap, at least a portion of the microparticles are fixed to the surface by exposing at least a portion of the surface of the implant or dental root and irradiating the surface and the microparticles with laser light in a state in which the microparticles are adhered to at least a portion of the surface.

According to this method, by fixing or sintering microparticles containing calcium on the surface of the implant or dental root, bonding strength between subsequently regenerated bone tissue and microparticles fixed to the implant or dental root can be enhanced. As a result, the implant or dental root can be immobilized on the regenerated alveolar bone more securely. In addition, if the surface of the implant is exposed when regeneration of bone tissue progresses, the activity of cells that form bone (such as osteoblasts) may decrease on the surface of the implant. However, as a result of modifying the surface of the implant using microparticles containing calcium, which demonstrates high biocompatibility, the activity of the aforementioned cells is enhanced and regeneration of bone tissue can be promoted.

The method for regenerating alveolar bone of the present invention is the method, wherein infected granulation tissue adhered in the gap is degenerated by irradiating the gap with the laser light prior to blowing the first air.

According to this method, since infected granulation tissue is degenerated in advance by irradiating with laser light, the efficiency at which the infected granulation tissue is removed by subsequently blowing the first air can be enhanced. In other words, infected granulation tissue can be removed more easily in comparison with the case of blowing the first air without irradiating with laser light.

The method for regenerating alveolar bone of the present invention is the method, wherein the microparticles are composed of carbonate apatite.

Since carbonate apatite, which is a type of apatite containing carbonic acid, is a material that has high biocompatibility, the use thereof makes it possible to further promote regeneration of bone tissue.

The method for regenerating alveolar bone of the present invention is the method, wherein the laser light is an Er:YAG laser.

The use of an Er:YAG laser (erbium YAG laser) makes it possible to efficiently degenerate the infected granulation tissue. Since adhesion of degenerated infected granulation tissue to an implant or alveolar bone decreases, the infected granulation tissue is more easily removed, thereby making this preferable. In addition, in the case of irradiating with laser light in the state in which the microparticles are adhered to at least a portion of the surface of the implant or dental root, Er:YAG laser light is absorbed by the microparticles at a higher rate in comparison with other laser light. In other words, the use of an Er:YAG laser enables the microparticles to be efficiently heated. Consequently, heating of the microparticles by irradiating with an Er:YAG laser and fixing or sintering the microparticles on the surface of the implant or dental root can be carried out more easily.

The method for regenerating alveolar bone of the present invention is the method, wherein the primary particle diameter of the microparticles is greater than 300 μm to 500 μm.

The use of the aforementioned microparticles having a primary particle diameter within this range makes it possible to further promote regeneration of alveolar bone.

The method for regenerating alveolar bone of the present invention is the method, wherein the microparticles are microparticles obtained by crushing clumps of raw material in a mortar.

The use of the aforementioned microparticles produced in the manner described above makes it possible to promote regeneration of alveolar bone even more.

The method for regenerating alveolar bone of the present invention is the method, wherein the microparticles are obtained by crushing clumps of raw material with a mortar followed by recovering those particles among the resulting particles that pass through a sieve (mesh) having a mesh size of 500 μm but do not pass through a sieve having a mesh size of 300 μm.

Use of the aforementioned microparticles produced in the manner described above makes it possible to promote regeneration of alveolar bone even more.

The method for regenerating alveolar bone of the present invention is the method, wherein the microparticles are mixed particles obtained by mixing particles having a primary particle diameter of greater than 300 μm to 500 μm and particles having a primary particle diameter of 10 μm or less.

Use of the aforementioned microparticles produced in the manner described above makes it possible to promote regeneration of alveolar bone even more.

The calcium-containing microparticles for regenerating alveolar bone of the present invention are calcium-containing microparticles used in the method for regenerating alveolar bone, and are obtained by crushing clumps of raw material composed of carbonate apatite followed by recovering those microparticles among the resulting microparticles that pass through a sieve (mesh) having a mesh size of 500 μm but do not pass through a sieve having a mesh size of 300 μm.

Filling these microparticles into a gap between alveolar bone and an implant or dental root makes it possible to promote regeneration of alveolar bone even more.

Effects of the Invention

According to the method for regenerating alveolar bone according to the present invention, treatment time can be shortened by promoting the formation of bone tissue between an implant or dental root and alveolar bone.

The calcium-containing microparticles for regenerating alveolar bone according to the present invention are able to promote regeneration of alveolar bone by filling the microparticles into a gap between alveolar bone and an implant or dental root.

BEST MODE FOR CARRYING OUT THE INVENTION

<Method for Regenerating Alveolar Bone>

The method for regenerating alveolar bone of the present invention is a method for regenerating alveolar bone in which bone tissue is regenerated in a gap between an implant or dental root and alveolar bone. The following provides an explanation of this method in the case of an implant with reference to FIGS. 1 to 4.

[Blowing of First Air]

Figure 1:
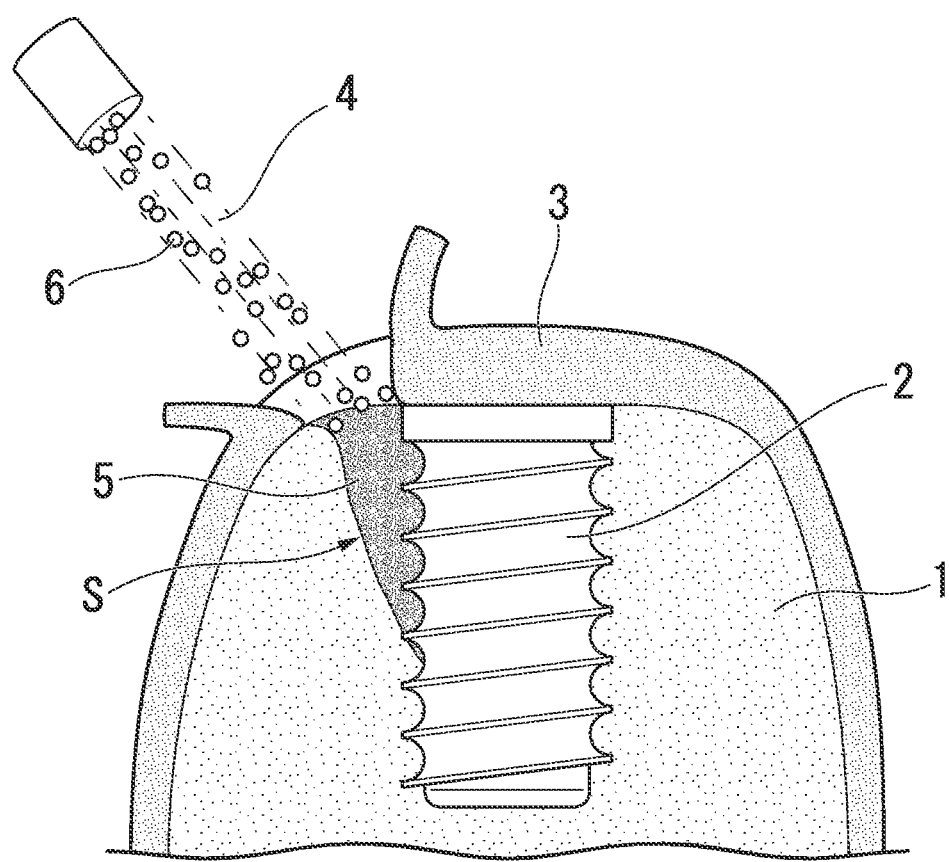
FIG. 1 is a longitudinal cross-sectional view of alveolar bone 1 showing a state in which a portion of infected granulation tissue 5 present in a gap S between the alveolar bone 1 and an implant 2 is removed in one example of an embodiment of the present invention.

First, as shown in FIG. 1, an incision is made in gingiva 3 surrounding an implant 2 embedded in alveolar bone 1, and a first air 4 is blown into a gap S between the implant 2 and the alveolar bone 1. A portion of infected granulation tissue 5 present in the gap S is removed by this blowing.

Preferably as much of the infected granulation tissue 5 as possible is removed at this stage. Microparticles 6 having calcium as a constituent thereof (to be simply referred to as microparticles 6) are preferably contained in the first air 4 in order to enhance the removal efficiency of the infected granulation tissue 5. The infected granulation tissue 5 can be worn off by allowing the microparticles 6 to collide with the infected granulation tissue 5. There are no particular limitations on the components of the first air 4, and air ordinarily used in dental care, such as dry air or nitrogen gas, can be used. Water may or may not be contained in the first air 4. Although there are no particular limitations on the pressure at which the first air 4 is blown, blowing at a pressure that damages the implant 2, gingiva 3 and alveolar bone 1 is preferably avoided.

Although a majority of the infected granulation tissue 5 present in the gap S can be removed by blowing the first air 4, it is difficult to completely remove all of the infected granulation tissue 5. It is particularly difficult to completely remove fine infected granulation tissue 5 that is difficult to be observed with the naked eye. Consequently, the infected granulation tissue 5 ends up remaining on a portion of the surface of the implant 2 or on a portion of the surface of the alveolar bone 1.

[Irradiation with Laser Light]

Figure 2:
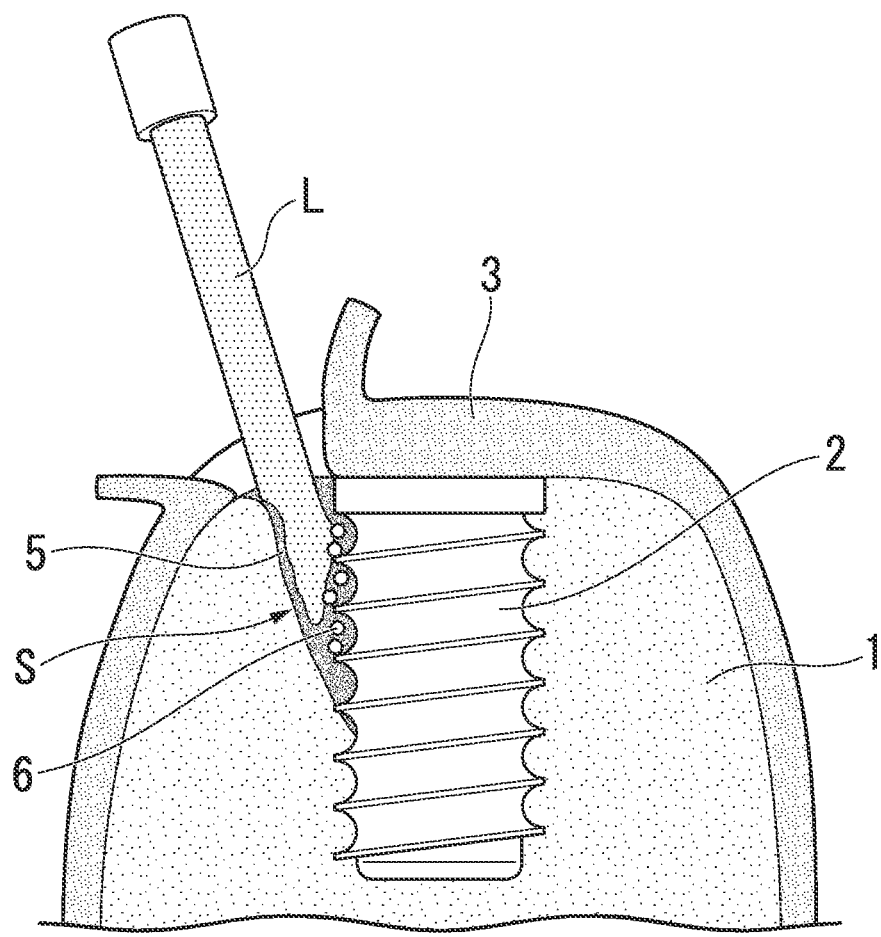
FIG. 2 is a longitudinal cross-sectional view of alveolar bone 1 showing a state in which a gap S is irradiated with laser light L following removal of a portion of infected granulation tissue 5 in one example of an embodiment of the present invention.

Next, as shown in FIG. 2, the gap S is irradiated with laser light L to degenerate the infected granulation tissue 5 remaining in the gap S. Since infected granulation tissue 5 that has been irradiated with the laser light L is incinerated by thermal degeneration or heat, it is easily removed from the surface of the implant 2 or the surface of the alveolar bone 1.

There are no particular limitations on the wavelength and intensity of the laser light L provided it is able to cause degeneration of the infected granulation tissue 5 with heat (thermal degeneration). Specific examples of the laser light L include an Er:YAG laser (erbium YAG laser) having a wavelength of about 2940 nm, an Nd:YAG laser (neodymium YAG laser) having a wavelength of about 1064 nm, an argon laser having a wavelength of about 488 nm, a semiconductor laser having a wavelength of about 655 nm to 2000 nm, a carbon dioxide gas laser having a wavelength of about 10600 nm, an Er:Cr:YSGG laser (erbium-chromium-YSGG laser) having a wavelength of about 2780 nm, and a helium neon laser having a wavelength of about 633 nm, all of which are ordinarily used in dental care.

Among these lasers, an Er:YAG laser is used preferably. The use of an Er:YAG laser makes it possible to degenerate the infected granulation tissue 5 as well as efficiently heat the microparticles 6 in the case of the microparticles 6 being adhered to the surface of the implant 2. This is because an Er:YAG laser is efficiently absorbed by the white microparticles 6 containing calcium. Heating of the microparticles 6 with an Er:YAG laser makes it possible to fix the microparticles 6 on the surface of the implant 2.

The following provides a further explanation of the aforementioned fixation.

In the present invention, in addition to containing the microparticles 6 in the first air 4 and blowing the first air 4 into the gap S to remove a portion of the infected granulation tissue 5 present in the gap S, by exposing at least a portion of the surface of the implant 2 with the microparticles 6 adhered to at least a portion of the aforementioned surface and irradiating the aforementioned surface and the aforementioned microparticles 6 with the laser light L, at least a portion of the aforementioned microparticles 6 is preferably fixed on at least a portion of the aforementioned surface.

There are no particular limitations on the method used to allow the microparticles 6 to remain on the surface of the exposed implant 2 from which the infected granulation tissue 5 has been removed by allowing them to adhere thereto or make contact therewith. Normally, if the surface of the implant 2 is exposed while removing the infected granulation tissue 5 by blowing the first air 4 into the gap S, the microparticles 6 are inevitably adhered to the aforementioned surface. The microparticles 6 remain on the surface of the implant 2 as long as the gap S is not aggressively cleaned using water or other cleaning liquid not containing the microparticles 6 for the purpose of removing the microparticles 6.

The aforementioned microparticles 6 can be fixed on the aforementioned surface by irradiating the aforementioned microparticles 6 and the aforementioned surface with the laser light L in a state in which the microparticles 6 remain on the aforementioned surface. The mechanism for this is presumed to involve melting of a portion of the surface of the microparticles 6 in contact with the surface of the implant 2 resulting in an increase in contact area (bonding area).

Bonding strength between bone tissue subsequently regenerated in the gap S and the microparticles 6 fixed to the implant 2 can be enhanced by fixing the microparticles 6 having calcium on the surface of the implant 2. The mechanism for this is presumed to involve the microparticles 6 being incorporated or fused within bone tissue due to the high level of biocompatibility between the bone tissue and calcium contained in the microparticles 6. As a result, the implant 2 can be more securely fixed to bone tissue of regenerated alveolar bone.

If the surface of the implant 2 is exposed when regeneration of bone tissue progresses in the gap S, the activity of cells that form bone (such as osteoblasts) may decrease on the surface of the implant 2. In order to prevent this problem, the surface of the implant 2 is preferably modified (by allowing the microparticles 6 to fix to the surface of the implant 2) by the microparticles 6 containing calcium having high biocompatibility. As a result of the aforementioned modification, activity relating to osteogenesis of the aforementioned cells can be enhanced and regeneration of bone tissue can be promoted.

[Blowing of Second Air]

Figure 3:
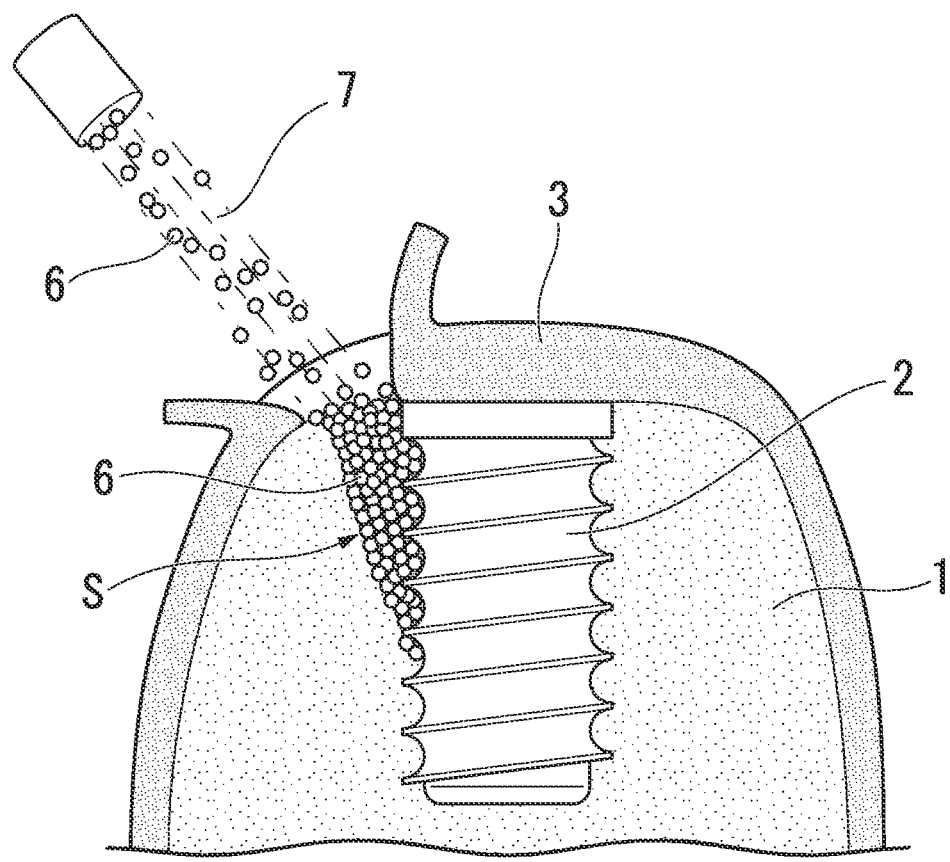
FIG. 3 is a longitudinal cross-sectional view of alveolar bone 1 showing a state in which microparticles 6 are filled into a gap S following irradiation with laser light L in one example of an embodiment of the present invention.
Figure 4:
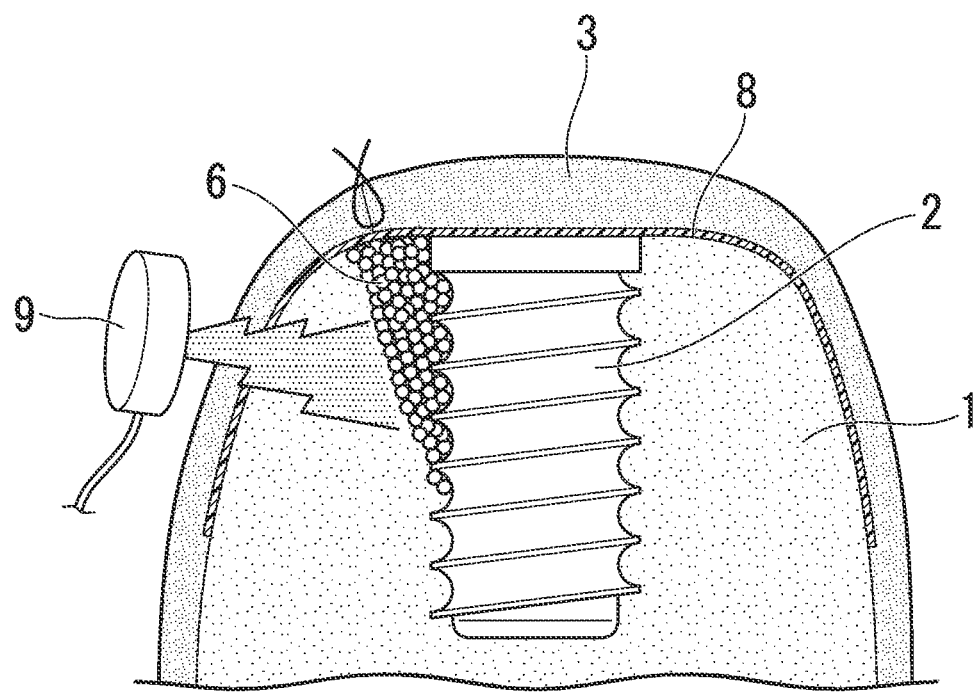
FIG. 4 is a longitudinal cross-sectional view of alveolar bone 1 showing a state in which a gap S filled with microparticles 6 is sutured and irradiated with ultrasonic waves in one example of an embodiment of the present invention.
Figure 5:
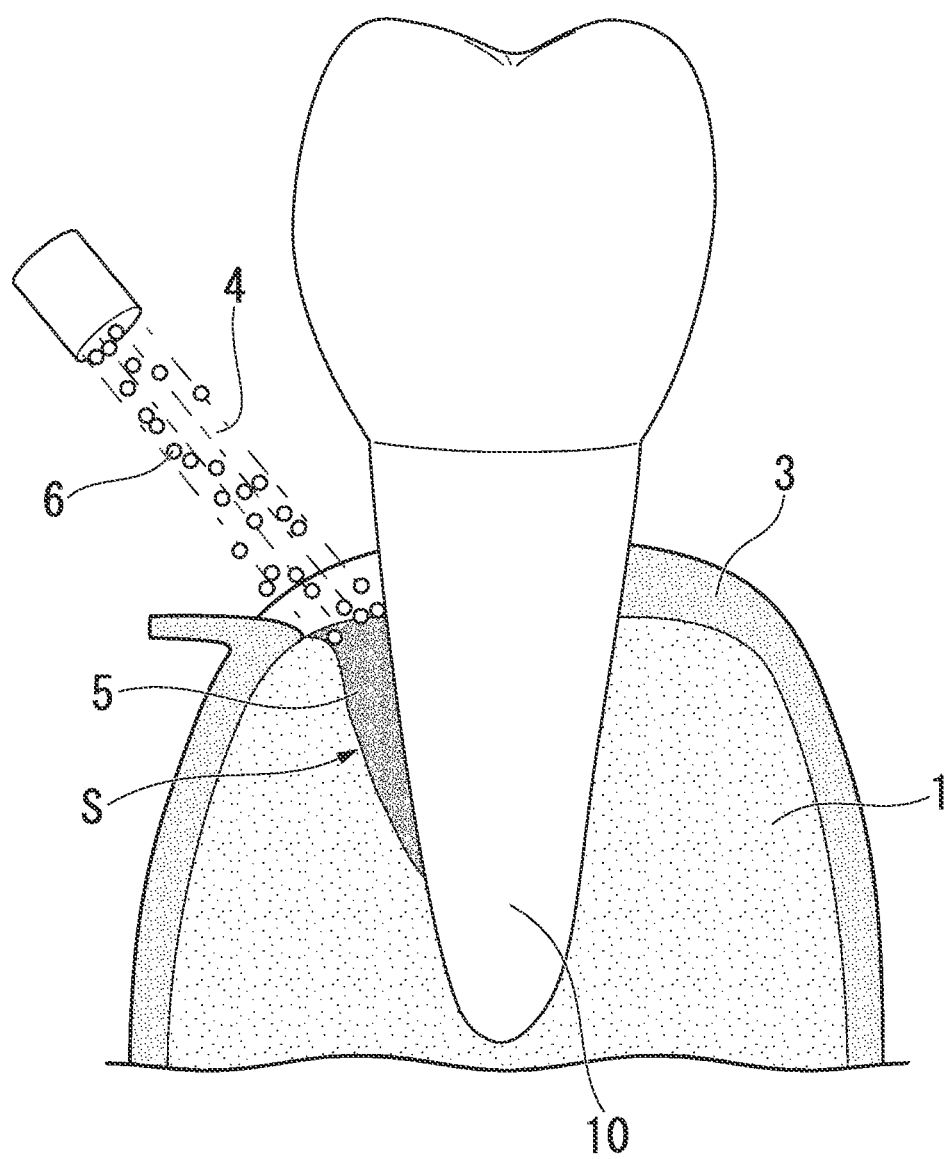
FIG. 5 is a longitudinal cross-sectional view of alveolar bone 1 showing a state in which a portion of infected granulation tissue 5 present in a gap S between the alveolar bone 1 and a dental root 10 is removed in another example of an embodiment of the present invention.
Figure 6:
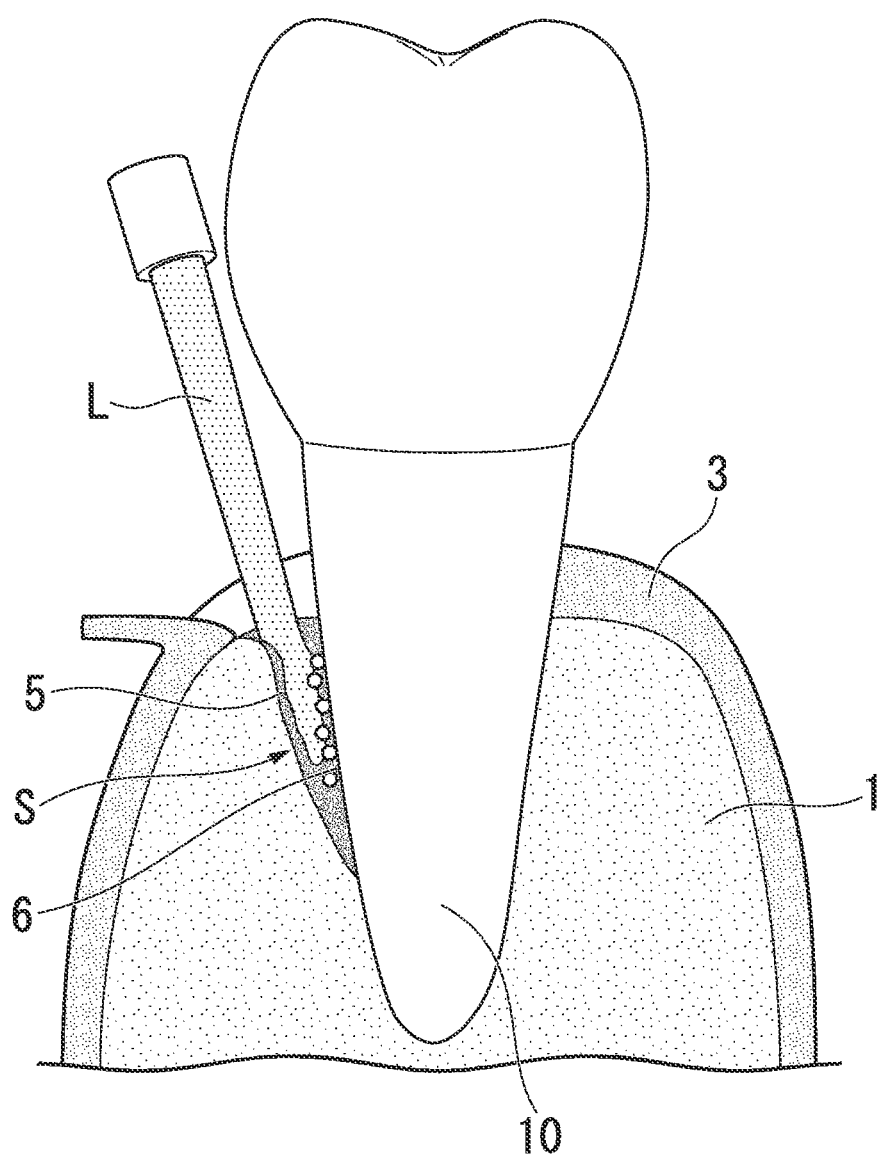
FIG. 6 is a longitudinal cross-sectional view of alveolar bone 1 showing a state in which a gap S is irradiated with laser light L following removal of a portion of infected granulation tissue 5 in another example of an embodiment of the present invention.
Figure 7:
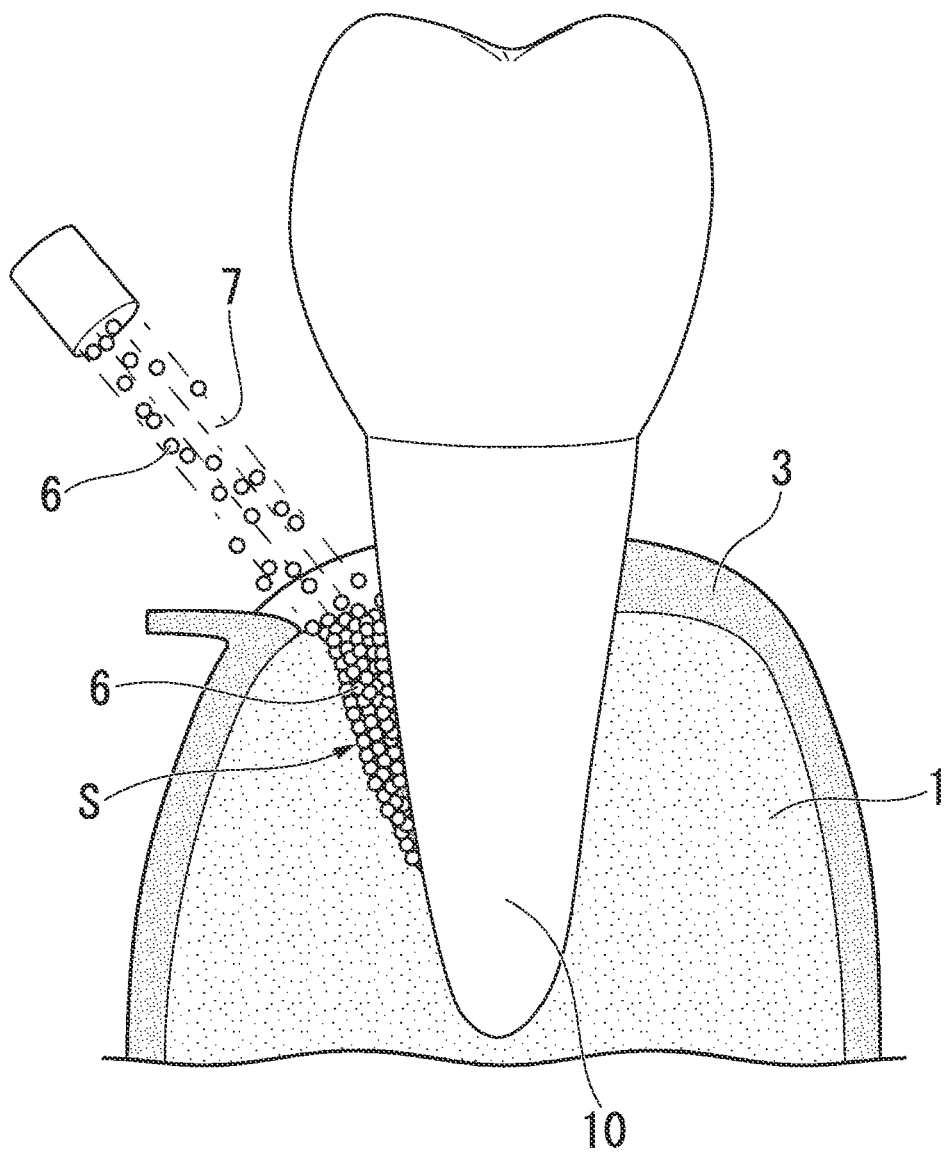
FIG. 7 is a longitudinal cross-sectional view of alveolar bone 1 showing a state in which microparticles 6 are filled into a gap S following irradiation with laser light L in another example of an embodiment of the present invention.
Figure 8:
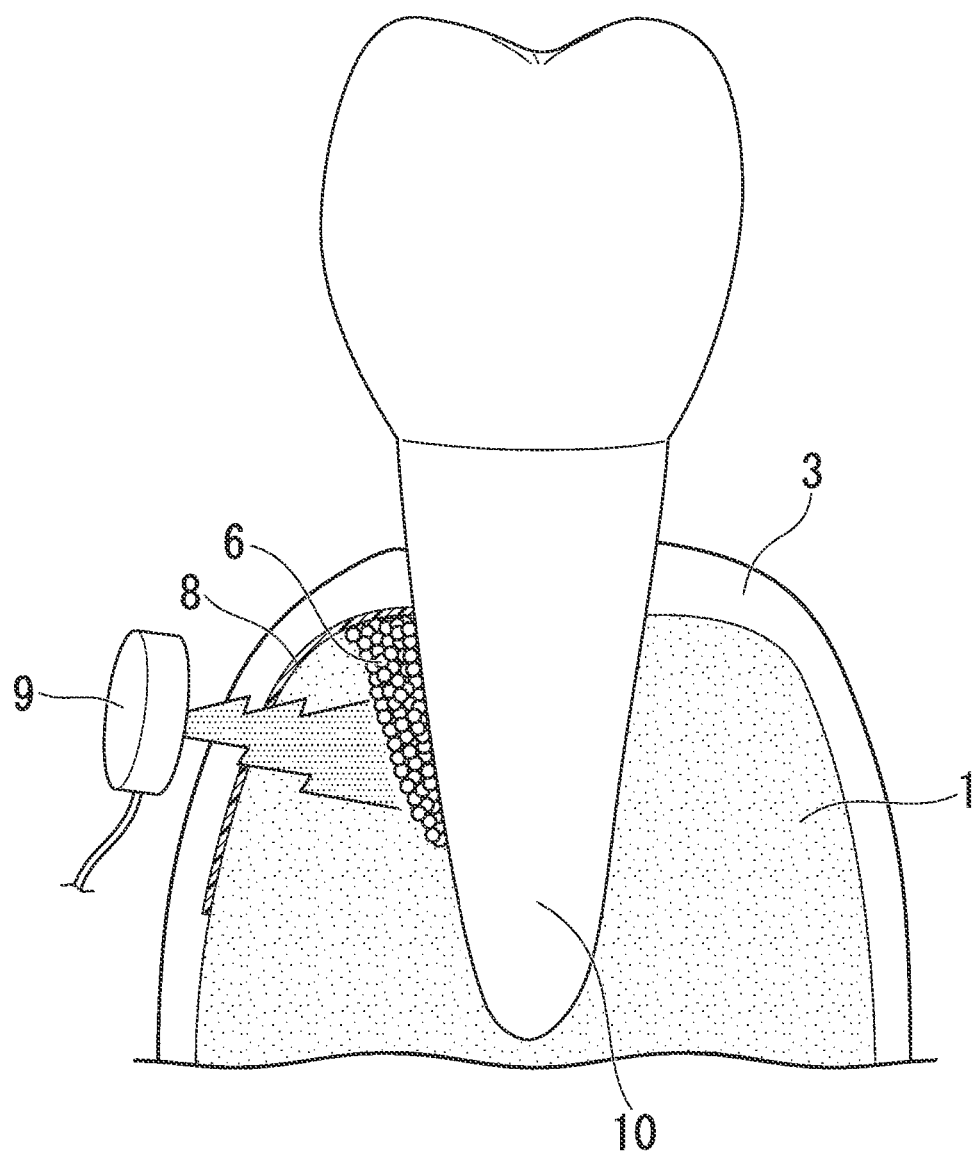
FIG. 8 is a longitudinal cross-sectional view of alveolar bone 1 showing a state in which a gap S filled with microparticles 6 is sutured and irradiated with ultrasonic waves in another example of an embodiment of the present invention.

Next, as shown in FIG. 3, a second air 7 containing the microparticles 6 and water is blown into the gap S after having irradiated the gap S with the laser light L to remove the aforementioned degenerated infected granulation tissue 5 and fill the inside of the gap S with the wet microparticles 6.

The microparticles 6 contained in the first air 4 or the second air 7 are preferably microparticles composed of carbonate apatite ($Ca_{10}(PO_4)CO_3$), apatite hydroxide ($Ca_{10}(PO_4)_6(OH)_2$) or β-tricalcium phosphate (β-TCP). Among these, carbonate apatite is able to further promote regeneration of solid (healthy) alveolar bone due to its particularly high level of biocompatibility, namely affinity for alveolar bone and affinity for cells involved in osteogenesis. The following provides a detailed explanation thereof.

Since the crystal structure and acid solubility of carbonate apatite are similar to those of natural bone, carbonate apatite is easily metabolized in the same manner as natural bone metabolism of alveolar bone. For example, carbonate apatite can be absorbed by osteoclasts. This property of being easily metabolized acts advantageously in the regeneration of alveolar bone. Moreover, since carbonate apatite has the property of enhancing the activity of osteoblasts, use of the microparticles 6 composed of carbonate apatite as a bone prosthetic material makes it possible to further promote regeneration of alveolar bone.

Regeneration of solid alveolar bone makes it possible to reliably immobilize the implant 2 and enhance its durability during subsequent use.

There are no particular limitations on the primary particle diameter of the microparticles 6 provided they are of a size that allows the microparticles 6 to be blown into the gap S in the case of being contained in the aforementioned air 4 and 7. The primary particle diameter of the microparticles 6 is preferably greater than 300 μm to 500 μm. If the primary particle diameter is within this range, the microparticles 6 are able to reach to the deepest portion of the gap S and efficiently remove the infected granulation tissue 5. Moreover, the microparticles 6 can also be filled into the deepest portion of the gap S. In addition, in the case of containing the microparticles 6 in the first air 4, exposing the surface of the implant 2 by removing the infected granulation tissue 5 and allowing the microparticles 6 to remain on the surface thereof can be carried out more easily.

In the case of blowing the first air 4 or the second air 7 containing the microparticles 6 and water (moisture), if the microparticles 6 preliminarily become wet prior to blowing, the microparticles 6 may flocculate, may become clogged in the blowing nozzle or become clogged at the entrance to the gap S. In order to avoid this flocculation, the microparticles 6 and water are preferably mixed in the air by spraying the water into the aforementioned air in a state in which the microparticles 6 in a dry state are dispersed in the air.

The water contained in the second air 7 preferably further contains a salt that composes a physiological salt solution, an antibiotic or a cytokine and the like. The containing of an antibiotic makes it possible to inhibit bacterial growth at the treatment site. The containing of a cytokine makes it possible to inhibit inflammation or enhance the activity of osteoblasts. The containing of a physiological salt makes it possible to adjust the aforementioned water to a composition similar to that of a physiological salt solution. As a result thereof, the infiltration of osteoblasts into the gap S filled with the microparticles 6 can be promoted and the formation of bone tissue in the gap S can be promoted.

[Protection of Gingiva]

The gap S is protected by suturing the incised gingiva 3 after having filled the gap S with the microparticles 6. At this time, a known film body 8 for guided bone regeneration (GBR) may be installed that protects the incision. The film body 8 is preferably removed at a suitable time during the course of osteogenesis.

After suturing the gingiva 3, the formation of bone tissue in the gap S is preferably promoted by contacting an ultrasonic apparatus 9 with the treatment site and generating ultrasonic waves using the method described in Patent Document 1.

Following the procedure as described above, the microparticles 6 filled into the gap S function as a bone prosthetic material and bone tissue is formed in the gap S by osteoblasts using the aforementioned microparticles 6 as scaffolds. As a result, the implant 2 can be immobilized in a desirable state by the generated alveolar bone 1.

As a result of applying the method for regenerating alveolar bone of the present invention, treatment time can be shorted by roughly half in comparison with conventional treatment methods in which radiation of the laser light L is not carried out. For example, in the case of treating a Japanese person age 50 to 60, although the treatment time for the lower jaw was about 3 months, that treatment time was able to be shortened to about 1 to 2 months when using the method of the present invention, and although the treatment time for the upper jaw was about 6 months, that treatment time was able to be shortened to about 2 to 3 months when using the method of the present invention.

<Microparticles Used in Method for Regenerating Alveolar Bone>

Although the aforementioned calcium-containing microparticles used in the method for regenerating alveolar bone according to the present invention may be microparticles obtained by a powder forming method (granulation method) such as spray drying, they are preferably microparticles obtained by crushing clumps of raw material in a mortar. Here, "crushing clumps of raw material in a mortar" refers to placing clumps composed of the same components as the aforementioned microparticles in a mortar and crushing or grinding the aforementioned clumps using a pestle of a size that is suitable for the mortar.

The aforementioned clumps of raw material are preferably composed of the same components or materials as the aforementioned microparticles, and there are no particular limitations on the shape thereof. The aforementioned clumps of raw material can be prepared by a known method for preparing dental materials.

There are no particular limitations on the size of the aforementioned clumps of raw materials and, for example, clumps can be used that have been formed to a size of about 0.1 cm to 10 cm. For example, the clumps can be placed in a mortar having a diameter of about 10 cm to 50 cm and crushed or ground using a suitable pestle. At this time, the aforementioned clumps may be crushed by hand using a pestle, or the aforementioned clumps may be crushed using an industrial crusher or grinder.

The aforementioned crushing treatment is preferably carried out until aggregates of particles obtained by crushing the aforementioned clumps of raw material contain a large number of microparticles having a primary particle diameter of 1 μm to 1000 μm.

Regeneration of alveolar bone can be promoted by using the aforementioned microparticles obtained by crushing the aforementioned clumps in the method for regenerating alveolar bone according to the present invention. One of the reasons for this is presumed to be that, since the microparticles have an irregular shape, the microparticles are easily incorporated into bone tissue by the activity of osteoclasts, osteoblasts and the like.

The aforementioned microparticles used in the method for regenerating alveolar bone according to the present invention are preferably microparticles obtained by crushing the aforementioned clumps of raw material followed by recovering those microparticles among the resulting microparticles that pass through a sieve having a mesh size of 500 μm but do not pass through a sieve having a mesh size of 300 μm.

The average primary particle diameter of microparticles recovered according to the aforementioned method is greater than 300 μm to 500 μm. In this case, the shape of the primary particles is not necessarily required to be spherical or roughly spherical, but rather individual particles may be irregular and have different shapes. The primary particle diameter of irregularly-shaped microparticles is the long diameter at which a line connecting two points on the surface of the microparticles is the longest. The average of the primary particle diameter of each irregularly-shaped microparticle is preferably greater than 300 μm to 500 μm.

The use of irregularly-shaped microparticles of this size makes it possible to further promote regeneration of alveolar bone. One reason for this is that, if the primary particle diameter of the aforementioned microparticles exceeds 300 μm, incorporation of the microparticles into bone tissue is carried out at a suitable rate, thereby making it possible to inhibit the induction of inflammation. In addition, another reason is that, if the primary particle diameter of the aforementioned microparticles is 500 μm or less, the microparticles are adequately incorporated into bone tissue making it possible to reduce the amount remaining as a foreign substance.

There are no particular limitations on the aforementioned method used to recover the aforementioned microparticles using a sieve, and recovery can be carried out using a known method. For example, commercially available sieves having the aforementioned mesh sizes are prepared, particles obtained by crushing the aforementioned clumps of raw material are placed on the sieve having the larger mesh size, the particles that pass through the sieve are placed on the sieve having the smaller mesh size, and those particles that remain on the sieve without passing through are recovered.

Mixed particles obtained by mixing large particles and small particles can be used for the aforementioned microparticles used in the method for regenerating alveolar bone according to the present invention. More specifically, mixed particles in which the primary particle diameter of the aforementioned large particles is greater than 300 μm to 500 μm and the primary particle diameter of the aforementioned small particles is 10 μm or less are preferable. The primary particle diameter of the aforementioned small particles is preferably greater than 1 μm.

Although there are no particular limitations thereon, the mixing ratio of the aforementioned mixed particles is preferably such that the weight ratio (weight of large particles/weight of small particles) is 1 to 100. In the case of this mixing ratio, the small particles can be adhered to the majority of the region (for example, about 60% to 90%) on the surface of the large particles that compose the mixed particles. In this manner, if a state results in which the large particles are coated with the small particles, regeneration of alveolar bone can be promoted, thereby making this preferable. This coated state can be confirmed by observing with an electron microscope.

Use of the aforementioned mixed particles makes it possible to promote regeneration of alveolar bone. One reason for this is presumed to be that, as a result of mixing the aforementioned small particles, cells such as osteoblasts or osteoclasts involved in the metabolism of bone tissue are activated, thereby promoting incorporation of the mixed particles into bone tissue.

As has been described above, a method for regenerating alveolar bone comprising the regeneration of bone tissue in a gap between an implant and alveolar bone has been explained with reference to FIGS. 1 to 4. This method can be similarly applied to the case of regenerating bone tissue in a gap between a dental root and alveolar bone and similar effects can be obtained. FIGS. 5 to 8 showing the method in the case of a dental root correspond to FIGS. 1 to 4 used to explain the method in the case of an implant. Since the same method as in the case of an implant can be carried out in the case of a dental root as well, a detailed explanation regarding the case of a dental root is omitted.

EXAMPLES

Preparation of Clumps of Raw Material

Clumps of carbonate apatite were synthesized as microparticle raw material in compliance with the method of the following Reference Document 1. More specifically, 2 liters of 2 molar calcium nitrate were dropped into 8 liters of 1.2 molar disodium phosphate solution containing 6 moles of disodium carbonate followed by synthesizing over the course of 3 days while automatically adjusting to pH 9.0±0.1 at a synthesis temperature of 100° C. (boiling). Washing with water and centrifugal separation treatment were repeatedly carried out on the sample obtained in the synthesis 10 times or more followed by drying. When the sample that had been adequately washed with water was analyzed by X-ray diffraction and infrared absorption spectrometry, the sample was confirmed to be carbonate apatite that was essentially free of impurities. Continuing, the dried sample was calcined using a commercially available heating apparatus. At this time, a calcined body was obtained by heating at a ramp rate of 5° C./min and holding at 500° C. for 1 hour. This calcined body was used as a carbonate apatite clump (raw material clump) in the experimental examples indicated below.

Reference Document 1

Doi, Y., Koda, T., Wakamatsu, N., Goto, T., Kamemizu, H., Moriwaki, Y., Adachi, M. and Suwa, Y.: Influence of carbonate on sintering of apatites, J. Dent. Res., 1993, 72:1279-1284.

Experimental Example 1

The prepared clump of carbonate apatite (diameter approx. 6 cm) was crushed in a mortar and the resulting crushed product was divided using a mesh having a mesh size of 500 μm and a mesh having a mesh size of 300 μm. More specifically, the following microparticles were prepared: (1) microparticles A composed of carbonate apatite having a primary particle diameter of greater than 300 μm to 500 μm, which passed through the mesh having a mesh size of 500 μm but did not pass through the mesh having a mesh size of 300 μm, (2) microparticles B composed of carbonate apatite having a primary particle diameter of greater than 500 μm, which did not pass through the mesh having a mesh size of 500 μm, and (3) microparticles C composed of carbonate apatite having a primary particle diameter of 300 μm or less which passed through both the mesh having a mesh size of 500 μm and the mesh having a mesh size of 300 μm. The primary particle diameter of each microparticle was confirmed with an electron microscope. The upper limit of the primary particle diameter of microparticles B was estimated to be about 1000 μm. In addition, the lower limit of the primary particle diameter of microparticles C was estimated to be about 0.1 μm to 1 μm.

Next, a total of 30 rats in which a bone defect having a diameter of 4 mm was formed in the skull were prepared, microparticles A were filled into the bone defects of 10 animals, microparticles B were filled into the bone defects of another 10 animals, and microparticles C were filled into the bone defects of the remaining 10 animals.

In histological evaluations performed 2 months later, newly formed bone was observed at the site of the bone defect in the group administered microparticles A, there was little carbonate apatite remaining that was not absorbed into the body, and inflammation was not observed. On the other hand, hardly any formation of new bone was observed at the site of the bone defect in the group administered microparticles B, and although carbonate apatite remained with hardly any being absorbed into the body, inflammation was not observed. In addition, there was hardly formation of new bone observed at the site of the bone defect in the group administered microparticles C, and severe inflammation was observed that was thought to have occurred due to excessively sudden absorption of microparticles C into the body.

On the basis of the results of Experimental Example 1, the newly-formed bone exhibiting regeneration of bone tissue was clearly determined to be greatly affected by the particle diameter of the administered microparticles. In other words, it was clearly determined that microparticles A, composed of carbonate apatite having a primary particle diameter of greater than 300 μm to 500 μm, are suitable for regeneration of bone tissue, and that the use of microparticles A makes it possible to promote regeneration of bone tissue in the form of alveolar bone and shorten treatment time.

Experimental Example 2

Microparticles D composed of carbonate apatite obtained by forming into a powder having a primary particle diameter of 300 μm to 500 μm using a granulation method commonly referred to as spray drying, and the microparticles A composed of carbonate apatite having a primary particle diameter of greater than 300 μm to 500 μm prepared in Experimental Example 1 were prepared. Each primary particle diameter was confirmed with an electron microscope.

Next, a total of 20 rats in which a bone defect having a diameter of 4 mm was formed in the skull were prepared, microparticles A were filled into the bone defects of 10 animals and microparticles D were filled into the bone defects of the remaining 10 animals. In histological evaluations performed 2 months later, significantly more newly formed bone was observed at the site of the bone defect in the group administered microparticles A, and there was significantly fewer microparticles B remaining at the site.

Although microparticles A and microparticles D have the same primary particle diameter, they have different shapes. Since microparticles D are microparticles formed by spray drying, they are roughly spherical, the shape is uniform for each particle, and the surface thereof is smooth. On the other hand, microparticles A are aggregates of irregularly-shaped particles formed by crushing clumps, the surface thereof is rough and their shape has surface irregularities and sharp corners. The microparticles A having these surface irregularities and sharp corners are thought to be easily metabolized by cells involved in the regeneration of bone tissue.

Based on the results of Experimental Example 2, the use of microparticles A that are easily absorbed into the body was clearly determined to make it possible to promote regeneration of alveolar bone more easily and shorten treatment time.

Experimental Example 3

The microparticles D formed in Experimental 2 were mixed with microparticles d composed of carbonate apatite having a primary particle diameter of 5 μm to 10 μm formed by spray drying to obtain microparticles E in which the microparticles d are adhered to the surface of the microparticles D. The mixing ratio between the microparticles D and the microparticles d was 1 part by weight to 10 parts by weight of microparticles d to 10 parts by weight of microparticles D.

Next, a total of 20 rats in which a bone defect having a diameter of 4 mm was formed in the skull were prepared, microparticles D were filled into the bone defects of 10 animals and microparticles E were filled into the bone defects of the remaining 10 animals. In histological evaluations performed 2 months later, significantly more newly formed bone was observed at the site of the bone defect in the group administered microparticles E, and there was significantly fewer microparticles E remaining at the site.

Although microparticles D and microparticles E have roughly the same primary particle diameters, the forms of their surfaces differ. Since the microparticles D are microparticles formed by spraying drying, they are roughly spherical, the shape is uniform for each particle, and the surface thereof is smooth. On the other hand, since microparticles E consist of microparticles d adhered to the surface of the microparticles D, the surface thereof is rough and their shape has surface irregularities. The microparticles E having these surface irregularities are thought to be easily metabolized by cells involved in the regeneration of bone tissue.

Based on the results of Experimental Example 3, the use of microparticles E that are easily absorbed into the body was clearly determined to make it possible to promote regeneration of alveolar bone more easily and shorten treatment time.

Experimental Example 4

A titanium base plate (circular base plate having a diameter of 10 mm and thickness of 2 mm) in compliance with JIS standards was prepared for use as a material corresponding to the body of an implant embedded in alveolar bone. After blasting the surface of the base plate with alumina having a grain size of 60 mesh at a pressure of 0.5 MPa for 10 minutes, the surface of the base plate was further subjected to glow discharge treatment in order to clean and roughen the surface. Subsequently, measurement of surface roughness using a Nanoscale Hybrid Microscope (VN-8010, Keyence Corp.) yielded a value of Ra=587.9±45.8 nm.

Next, 0.4 mL of distilled water were added to 100 mg of clumps of the prepared carbonate apatite, and a slurry obtained by crushing and mixing in an agate mortar was coated onto the surface of the prepared base plate at a thickness of 0.15 mm.

Continuing, the coated slurry and base plate surface were irradiated with a laser for 1 second each using an Er:YAG laser (Erwin AdvErL, Morita Corp.) and a C800F contact tip (quartz tip in the form of a flat tip having a diameter of 800 µm) in a non-contact state (positioned at a distance of 1 mm from the titanium base plate) and in the absence of water injection under conditions of a panel value of 150 mJ/pulse and 10 pps. At this time, measurement of the temperature of the laser-irradiated site revealed that the temperature did not exceed 53° C., which is the threshold temperature for the occurrence of irreversible changes in bone.

After washing the surface of the base plate following laser irradiation by spraying with distilled water using a syringe, ultrasonic cleaning was carried out for 10 minutes in a state in which the base plate was immersed in distilled water followed by further cleaning by immersing in distilled water at 37° C. for 24 hours and drying. After drying, the surface of the base plate was analyzed with a scanning electron microscope (SEM, osmium coating method), an electron probe microanalyzer (EPMA) and by infrared spectroscopy.

As a result of observing the surface with the SEM, although the surface of the base plate not coated with the slurry exhibited a coarse porous structure prior to laser irradiation, the surface was observed to have become smooth following laser irradiation. This is thought to be due to the surface of the base plate having melted at the laser-irradiated site. In addition, microparticles were observed to have become fixed at those sites coated with slurry and irradiated with laser light.

As a result of analyzing the surface with an EPMA, the presence of calcium and phosphorous was detected at those sites coated with slurry and irradiated with laser light. In addition, as a result of analyzing the surface by infrared spectrometry, since a peak characteristic of lowly crystalline apatite containing carbonate ions was detected at those sites coated with slurry and irradiated with laser light, microparticles composed of carbonate apatite were able to be confirmed to have adhered to the surface of the base plate.

Next, after cleaning the base plate with distilled water after coating with slurry and irradiating with laser light, the base plate was immersed in 60 mL of simulated body fluid (SBF) adjusted to pH 7.4 and held therein for 2 days or 7 days at 37° C. Subsequently, the surface of a freeze-dried sample was analyzed with an SEM and EPMA.

As a result of observing with the SEM, nuclei of crystals thought to be composed of carbonate apatite were observed to have precipitated in the sample held for 2 days, and the crystal nuclei were observed to have grown in the sample held for 7 days. In addition, the crystals were confirmed to contain calcium and phosphorous with the EPMA.

On the other hand, in a control sample not irradiated with laser light, namely on the surface of a titanium base plate to which microparticles were not adhered, precipitation of crystal nuclei was not observed and precipitation of bone-like apatite was not observed.

The aforementioned SBF is a solution containing inorganic ions such as $Na^+$, $K^+$, $Mg^{2+}$, $Ca^{2+}$, $Cl^-$, $HCO_3^-$, $HPO_4^{2-}$ or $SO_4^{2-}$ that has components similar to those of human serum, and was prepared in compliance with the following Reference Document 2.

Reference Document 2

Kokubo, T., Kushitani, H., Sakka, S., Kitsugi, T. and Yamamuro, T.: Solutions able to reproduce in vivo surface-structure changes in bioactive glass-ceramic A-W. J. Biomed. Mater. Res., 1990, 24:721-734.

In Experimental Example 4, as a result of laser-irradiating the surface of an implant or dental root in a state of having microcrystals composed of carbonate apatite adhered thereto, the microparticles were confirmed to be able to become securely fixed to the surface of the implant or dental root. Moreover, on the surface of the implant or dental root having the microparticles adhered thereto, crystals of bone-like apatite at least containing calcium and phosphorous were in a state in which they easily precipitate and grow in an environment resembling that of the human body, and the crystals were confirmed to grow over time.

On the basis of these results, adhering microcrystals containing calcium to the surface of an implant or dental root at a treatment site by irradiating with laser light was clearly determined to make it possible to promote regeneration of alveolar bone and shorten treatment time.

Although the above has provided a detailed description of an embodiment of the present invention with reference to the drawings, the specific configuration thereof is not limited to this embodiment, but rather design changes and the like are also included within a range that does not deviate from the gist of the present invention.

INDUSTRIAL APPLICABILITY

The present invention can be used in surgery performed by a dental surgeon for regenerating alveolar bone by removing infected granulation tissue that has formed around an implant embedded in alveolar bone or around a dental root that has been affected by pyorrhea and the like.

BRIEF DESCRIPTION OF THE REFERENCE SYMBOLS

1 Alveolar bone
2 Implant
3 Gingiva
4 First air
5 Infected granulation tissue
6 Microparticles having calcium as a constituent thereof
7 Second air
8 Film body for GBR
9 Ultrasonic apparatus
10 Dental root S Gap
L laser light

The invention claimed is:

1. A method for regenerating alveolar bone in which bone tissue is regenerated in a gap between an implant or dental root and alveolar bone, comprising: a procedure consisting of making an incision in the gingiva surrounding an implant or dental root embedded in alveolar bone, blowing a first air into a gap between the implant or dental root and the alveolar bone to remove a portion of infected granulation tissue present in the gap, and irradiating the gap with laser light to degenerate the infected granulation tissue remaining in the gap, followed by blowing a second air containing microparticles having calcium as a constituent thereof and water into the gap to remove the degenerated infected granulation tissue and fill in the gap with the wet microparticles.

2. The method for regenerating alveolar bone according to claim 1, wherein together with containing microparticles in the first air and blowing the first air into the gap to remove a portion of infected granulation tissue present in the gap, at least a portion of the microparticles are fixed to the surface by exposing at least a portion of the surface of the implant or dental root and irradiating the surface and the microparticles with laser light in a state in which the microparticles are adhered to at least a portion of the surface.

3. The method for regenerating alveolar bone according to claim 1, wherein infected granulation tissue adhered in the gap is degenerated by irradiating the gap with the laser light prior to blowing the first air.

4. The method for regenerating alveolar bone according to claim 1, wherein the microparticles are composed of carbonate apatite.

5. The method for regenerating alveolar bone according to claim 1, wherein the laser light is an Er:YAG laser.

6. The method for regenerating alveolar bone according to claim 1, wherein the primary particle diameter of the microparticles is greater than 300 µm to 500 µm.

7. The method for regenerating alveolar bone according to claim 1, wherein the microparticles are microparticles obtained by crushing clumps of raw material in a mortar.

8. The method for regenerating alveolar bone according to claim 1, wherein the microparticles are obtained by crushing clumps of raw material with a mortar followed by recovering those particles among the resulting particles that pass through a sieve having a mesh size of 500 µm but do not pass through a sieve having a mesh size of 300 µm.

9. The method for regenerating alveolar bone according to claim 1, wherein the microparticles are mixed particles obtained by mixing particles having a primary particle diameter of greater than 300 µm to 500 µm and particles having a primary particle diameter of 10 µm or less.

* * * * *